United States Patent
Cox et al.

[19]

[11] Patent Number: 5,997,851
[45] Date of Patent: Dec. 7, 1999

[54] HAIR CARE COMPOSITIONS CONTAINING LOW MELTING POINT FATTY ALCOHOL AND ETHYLENE OXIDE/PROPYLENE OXIDE POLYMER

[75] Inventors: Bruce Russell Cox, West Chester, Ohio; Michael Thomas Dodd, Edgewood, Ky.

[73] Assignee: The Procter & Gamble Company, Cincinnati, Ohio

[21] Appl. No.: 08/743,397

[22] Filed: Nov. 4, 1996

Related U.S. Application Data

[63] Continuation of application No. 08/605,656, Feb. 22, 1996, abandoned, which is a continuation of application No. 08/357,646, Dec. 22, 1994, abandoned, which is a continuation-in-part of application No. 08/190,830, Feb. 2, 1994, abandoned.

[51] Int. Cl.$^6$ ........................................ A61K 7/08
[52] U.S. Cl. .................. 424/70.1; 424/70.12; 424/70.19; 424/70.27; 424/70.28
[58] Field of Search ................ 424/70.1, 70.12, 424/70.19, 70.27, 70.28

[56] References Cited

U.S. PATENT DOCUMENTS

| | | | |
|---|---|---|---|
| 3,687,855 | 8/1972 | Halpern | 252/106 |
| 4,387,090 | 6/1983 | Bolich, Jr. | 424/70 |

FOREIGN PATENT DOCUMENTS

| | | |
|---|---|---|
| 0 262 885 | 4/1988 | European Pat. Off. . |
| 0 473 349 B1 | 3/1992 | European Pat. Off. . |
| 1961 152 | 6/1970 | Germany . |
| 201839 | 8/1993 | Japan . |
| 5201841 | 8/1993 | Japan . |
| 2218334 | 11/1989 | United Kingdom . |
| WO 91/16878 | 11/1991 | WIPO . |

*Primary Examiner*—Jyothsna Venkat
*Attorney, Agent, or Firm*—William J. Winter

[57] ABSTRACT

The present invention relates to hair conditioning compositions comprising from about 0.1% to about 10% by weight of a monohydric, fatty alcohol having a melting point of 30° C. or lower; from about 0.1% to about 10%, by weight of a polymer of ethylene oxide, propylene oxide, and mixtures thereof, having the general formula:

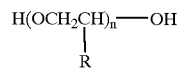

wherein R is selected from the group consisting of H, methyl, and mixtures thereof; and n has an average value of from about 2,000 to about 14,000; from 0% to about 20%, by weight, of a conditioning agent selected from the group consisting of cationic surfactants, cationic polymers, nonvolatile silicones, nonvolatile hydrocarbons, saturated $C_{14}$ to $C_{22}$ straight chain fatty alcohols, nonvolatile hydrocarbon esters, and mixtures thereof; and water. These hair care compositions provide a product with a thickened, cream emulsion or gel-type rheology having good wet hair feel, spreadability, and rinseability, as well as providing glossiness, hair alignment, volume reduction, and dry combing benefits.

23 Claims, No Drawings

HAIR CARE COMPOSITIONS CONTAINING LOW MELTING POINT FATTY ALCOHOL AND ETHYLENE OXIDE/PROPYLENE OXIDE POLYMER

This is a continuation of application Ser. No. 08/605,656, filed on Feb. 22, 1996, now abandoned, which is a continuation of application Ser. No. 08/357,646, filed on Dec. 22, 1994 now abandoned, which is a continuation in part of application Ser. No. 08/190,830, filed on Feb. 2, 1994 (abandoned).

TECHNICAL FIELD

The present invention relates to hair care compositions such as cream rinse emulsions, that enhance glossiness of the hair and provide dry combing benefits, containing low melting point fatty alcohols and particular water soluble, nonionic polymers.

BACKGROUND OF THE INVENTION

Scalp hair becomes soiled due to its contact with the surrounding environment and from sebum secreted from the hair follicles. The build-up of sebum and environmental soiling can cause the hair to have a dirty or greasy feel, and an unattractive appearance. In order to ameliorate these effects, it is necessary to shampoo the hair with regularity.

Shampooing the hair removes excess sebum and other environmental soiling but has disadvantages in that the hair can be left in a wet, tangled, and relatively unmanageable state. Shampooing can also result in the hair becoming dry due to the removal of natural oils or other hair moisturizing materials. After shampooing, the hair can also suffer from a perceived loss of "softness." Frequent shampooing also contributes to the phenomena of "split ends," particularly for long hair. Split ends refers to a condition wherein the ends of the hair are split into two or more shafts, resulting in a frizzy appearance.

A variety of approaches have been developed to condition the hair. These range from post-shampooing hair rinses, to leave-on hair conditioners, to the inclusion of hair conditioning components in shampoos. Although many consumers prefer the ease and convenience of a shampoo which includes conditioners, a substantial proportion of consumers prefer the more conventional conditioner formulations which are applied to the hair as a separate step from shampooing, usually subsequent to shampooing. These hair conditioners typically are formulated as a thickened product, such as a gel or cream, for ease of dispensing and application to the hair.

Consumers who have naturally coarse, wavy, or curly hair and wish to reduce these natural tendencies, may prefer conditioners which provide shine, hair alignment, and decreased hair volume. In addition some consumers who have relatively straight hair desire volume reduction and greater alignment of the hair for enhanced glossiness and an orderly appearance of the hair.

Hair shine or "glossiness" is a desirable attribute which refers to the contrast between the specular and diffuse light reflected off hair fibers. This contrast creates a visual perception of "sheen" strongly associated with healthy hair. A conventional method for increasing hair shine is to treat the hair with compositions containing hydrocarbon oils and fatty esters. Unfortunately, while these types of materials are effective for achieving their intended effect, they also tend to leave the hair feeling greasy or oily, and cause the hair to resoil relatively quickly.

Improved glossiness, hair alignment, and volume reduction with relatively little greasy or oily feel when applied to the hair at relatively low levels, can be obtained in hair care formulations through the use of low melting point fatty alcohols. Low melting point fatty alcohols include, for example a variety of branched chain alcohols, short chain alcohols such as those having $C_8$ to $C_{12}$ chain length, and unsaturated straight chain alcohols such as oleyl alcohol. Despite these advantages, some low melting point fatty alcohols do not form the thick, gel rheology with cationic surfactants as do the saturated straight chain fatty alcohols, and low melting point fatty alcohols may reduce wet hair feel.

Hair rinse conditioners have conventionally been based on the combination of a cationic surfactant, which is generally a quaternary ammonium compound such as ditallow dimethyl ammonium chloride, and fatty alcohols, such as cetyl and stearyl alcohols. This combination results in a gel-network structure which provides the compositions with a thick, creamy rheology. However, low melting point fatty alcohols do not form the thick, gel rheology with cationic surfactants as do the saturated straight fatty alcohols, such as cetyl and stearyl alcohols. When a combination of low melting point and waxy alcohols are used, a hair volumizing effect may occur rather than volume reduction and increased alignment. This is because fatty alcohols for hair conditioning, such as cetyl and stearyl alcohols, deposit on the hair in crystal or solid form. These crystalline deposits separate the hair follicles to provide a volumizing effect. The net effect is reduced glossiness.

In addition some low melting fatty alcohols, e.g. oleyl alcohol, reduces the consumer preferred pleasing wet hair feel and perception of spreading through the hair that is provided by conventional creme hair rinses.

It has now been found that hair conditioning compositions can be provided in the form of a product with a thickened, cream emulsion or gel-type rheology having excellent wet hair feel, spreadability, and rinseability, as well as providing glossiness, hair alignment, and volume reduction, and especially dry combing benefits, through the use of certain low melting point fatty alcohols plus certain water soluble, nonionic, polyoxyethylene and/or polyoxypropylene polymers. In addition selection of particular polyoxyethylene and/or polyoxypropylene polymers having the molecular weights outlined below, also minimizes formulation problems, e.g. stringiness. The invention hereof is described in the sections below.

It is an object of this invention to provide hair care compositions that enhance hair shine and hair alignment, and can reduce hair volume, without causing the hair to become greasy or waxy feeling or to have a dirty or coated appearance.

It is desirable to provide such a composition, as described above in a thickened form, such as a cream emulsion or gel, which can be easily applied and rinsed from the hair. It is a further object of this invention to provide such a hair care composition that has an aesthetically pleasing wet hair feel and perception of spreading upon application to the hair, and especially has dry combing advantages.

It is further desirable to provide a method for conditioning hair in accordance with the above compositions.

These and other objects and benefits of the present invention as may be set forth herein as may now or later become apparent to those skilled in the art can be provided according to the invention which is described herein.

The invention hereof can comprise, consist of, or consist essentially of the essential elements described herein as well as any of the preferred or other optional ingredients described herein.

All percentages herein are by weight of the composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials which may be combined with the ingredient in commercially available products.

All documents referred to herein, including all patents, all patent applications and all articles, are hereby incorporated herein by reference in their entirety unless otherwise indicated.

SUMMARY OF THE INVENTION

The present invention relates to hair care compositions that provide enhanced gloss, alignment, and dry combing, as well as volume reduction to the hair, with low or reduced greasy, oily hair feel, while being formulated in an emulsion having a thick, cream-type rheology with excellent spreading, perception of spreading, and wet hair feel. In particular, the present hair care composition comprises:

(a) from about 0.1% to about 10%, by weight, preferably from about 0.1% to about 5%, more preferably from about 0.25% to about 1%, of a monohydric, fatty alcohol having a melting point of 30° C. or lower;

(b) from about 0.1% to about 10%, by weight, preferably from about 0.2% to about 5%, more preferably from about 0.5% to about 3%, of a polymer of ethylene oxide, propylene oxide, and mixtures thereof, having the general formula:

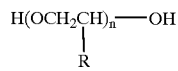

wherein R is selected from the group consisting of H, methyl, and mixtures thereof; and n has an average value of from about 2,000 to about 14,000, preferably from about 5,000 to about 9,000, more preferably from about 6,000 to about 8,000;

(c) from 0% to about 20%, by weight, of a conditioning agent selected from the group consisting of cationic surfactants, cationic polymers, nonvolatile silicones, nonvolatile hydrocarbons, saturated $C_{14}$ to $C_{22}$ straight chain fatty alcohols, nonvolatile hydrocarbon esters, and mixtures thereof; and (d) from about 50% to about 99.8%, by weight, water.

The present invention also relates to methods for conditioning hair by applying of an effective amount of the composition to the hair.

DETAILED DESCRIPTION OF THE INVENTION

The present invention relates to a hair conditioning composition comprising:

(a) from about 0.1% to about 10%, by weight, preferably from about 0.1% to about 5%, more preferably from about 0.25% to about 1%, of a monohydric, fatty alcohol having a melting point of 30° C. or lower, said fatty alcohol being preferably selected from the group consisting of unsaturated straight chain fatty alcohols, saturated branched chain fatty alcohols, saturated $C_8$–$C_{12}$ straight chain alcohols, and mixtures thereof;

(b) from about 0.1% to about 10%, by weight, preferably from about 0.2% to about 5%, more preferably from about 0.5% to about 3%, of a polymer of ethylene oxide, propylene oxide, and mixtures thereof, having the general formula:

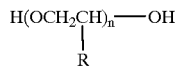

wherein R is selected from the group consisting of H, methyl, and mixtures thereof; and n has an average value of from about 2,000 to about 14,000, preferably from about 5,000 to about 9,000, more preferably from about 6,000 to about 8,000;

(c) from 0% to about 20%, by weight, of a conditioning agent selected from the group consisting of cationic surfactants, cationic polymers, nonvolatile silicones, nonvolatile hydrocarbons, saturated $C_{14}$ to $C_{22}$ straight chain fatty alcohols, nonvolatile hydrocarbon esters, and mixtures thereof; and (d) from about 50% to about 99.8%, by weight, water.

The essential ingredients as well as a variety, but nonexclusive, list of preferred and optional ingredients are described below.

NONVOLATILE, LOW MELTING POINT FATTY ALCOHOL

The compositions of the present invention comprise from about 0.1% to about 10%, by weight, preferably from about 0.1% to about 5%, more preferably from about 0.25% to about 1%, of a nonvolatile low melting point fatty alcohol.

The fatty alcohols hereof have a melting point of 30° C. or less, preferably about 25° C. or less, more preferably about 22° C. or less.

The unsaturated fatty alcohols hereof are also nonvolatile. By nonvolatile what is meant is they have a boiling point at 1.0 atmospheres of at least about 260° C., preferably at least about 275° C., more preferably at least about 300° C.

Suitable fatty alcohols include unsaturated monohydric straight chain fatty alcohols, saturated branched chain fatty alcohols, saturated $C_8$–$C_{12}$ straight chain fatty alcohols, and mixtures thereof. The unsaturated straight chain fatty alcohols will typically have one degree of unsaturation. Di- and tri- unsaturated alkenyl chains may be present at low levels, preferably less than about 5% by total weight of the unsaturated straight chain fatty alcohol, more preferably less than about 2%, most preferably less than about 1%.

Preferably, the unsaturated straight chain fatty alcohols will have an aliphatic chain size of from $C_{12}$–$C_{22}$, more preferably from $C_{12}$–$C_{18}$, most preferably from $C_{16}$–$C_{18}$. Especially preferred alcohols of this type include oleyl alcohol and palmitoleic alcohol.

The branched chain alcohols will typically have aliphatic chain sizes of from $C_{12}$–$C_{22}$, preferably $C_{14}$–$C_{20}$, more preferably $C_{16}$–$C_{18}$. Exemplary branched chain alcohols for use herein include isostearyl alcohol, octyl dodecanol, and octyl decanol.

Examples of saturated $C_8$–$C_{12}$ straight chain alcohols include octyl alcohol, caprylic alcohol, decyl alcohol, and lauryl alcohol.

The low melting point fatty alcohols hereof are used at a level of from about 0.1% to about 10%, by weight of the composition, more preferably from about 0.1% to about 5%, most preferably from about 0.25% to about 1%.

The present compositions are preferably limited to levels of monohydric saturated straight chain fatty alcohols, such as cetyl alcohol and stearyl alcohol, and other waxy fatty alcohols having melting points above 45° C., of no more than about 5%, by weight of the composition, preferably no more than about 4% since the presence of such waxy fatty alcohols can adversely affect the shine benefits of the present invention. However, it may be desirable to use waxy fatty alcohols for their conditioning benefits.

WATER SOLUBLE, NONIONIC, POLYMERS OF ETHYLENE OXIDE AND PROPYLENE OXIDE

The compositions of the present invention comprise from about 0.1% to about 10%, more preferably from about 0.2% to about 5%, and most preferably from about 0.5% to about 3% of a polymer of ethylene oxide and/or propylene oxide.

The polymers of the present invention are characterized by the general formula:

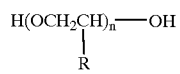

wherein R is selected from the group consisting of H, methyl, and mixtures thereof. When R is H, these materials are polymers of ethylene oxide, which are also known as polyethylene oxides, polyoxyethylenes, and polyethylene glycols.

When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from about 2,000 to about 14,000, preferably from about 5,000 to about 9,000, more preferably from about 6,000 to about 8,000.

Polyethylene glycol polymers useful herein that are especially preferred are PEG-2M wherein R equals H and n has an average value of about 2,000 (PEG 2-M is also known as Polyox WSR® N-10 from Union Carbide and as PEG-2,000); PEG-5M wherein R equals H and n has an average value of about 5,000 (PEG 5-M is also known as Polyox WSR® N-35 and Polyox WSR® N-80, both from Union Carbide and as PEG-5,000 and Polyethylene Glycol 300,000); PEG-7M wherein R equals H and n has an average value of about 7,000 (PEG 7-M is also known as Polyox WSR® N-750 from Union Carbide); PEG-9M wherein R equals H and n has an average value of about 9,000 (PEG 9-M is also known as Polyox WSR® N-3333 from Union Carbide); and PEG-14 M wherein R equals H and n has an average value of about 14,000 (PEG 14-M is also known as Polyox WSR® N-3000 from Union Carbide.)

Other useful polymers include the polypropylene glycols and mixed polyethylene/polypropylene glycols.

All percentages describing the polymers in this section of the description herein, are by weight, unless otherwise specified.

WATER

The compositions of the present invention comprise from about 50% to about 99.8%, by weight, water. The water phase can optionally include other liquid, water-miscible or water-soluble solvents such as lower alkyl alcohols, e.g. $C_1$–$C_5$ alkyl monohydric alcohols, preferably $C_2$–$C_3$ alkyl alcohols. However, the liquid fatty alcohol must be miscible in the aqueous phase of the composition. Said fatty alcohol can be naturally miscible in the aqueous phase or can be made miscible through the use of cosolvents or surfactants.

The composition of the present invention is an emulsion, having viscosity at 25° C. of at least about 5,000 cP preferably from about 8,000 cP to about 50,000 cP, more preferably from about 15,000 cP to about 35,000 cP. Viscosity is determined by a Brookfield RVT, at 20 RPM.

The compositions of the present invention preferably have a pH of from about 2.5 to about 7, more preferably from about 3 to about 6.8, most preferably from about 3.5 to about 6.5. Higher pH can be utilized as long as the composition retains a viscosity of at least about 8,000 cP at 25° C.

ADDITIONAL CONDITIONING AGENTS

The compositions of the present invention can also comprise one or more additional conditioning agents, such as those selected from the group consisting of cationic surfactants, cationic polymers, nonvolatile silicones (including soluble and insoluble silicones), nonvolatile hydrocarbons, saturated $C_{14}$ to $C_{22}$ straight chain fatty alcohols, nonvolatile hydrocarbon esters, and mixtures thereof. Preferred conditioning agents are cationic surfactants, cationic polymers, saturated $C_{14}$ to $C_{22}$ straight chain fatty alcohols, and silicones (especially insoluble silicones). The components hereof can comprise from 0% to about 20%, preferably, from about 0.1% to about 20%, more preferably from about 0.5% to about 10%, of additional conditioning agents.

CATIONIC SURFACTANTS

Cationic surfactants useful in compositions of the present invention, contain amino or quaternary ammonium moieties. The cationic surfactant will preferably, though not necessarily, be insoluble in the compositions hereof. Cationic surfactants among those useful herein are disclosed in the following documents, all incorporated by reference herein: M.C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

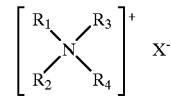

wherein $R_1$–$R_4$ are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated. Especially preferred are di-long chain (e.g., di $C_{12}$–$C_{22}$, preferably $C_{16}$–$C_{18}$, aliphatic, preferably alkyl). di-short chain (e.g., $C_1$–$C_3$ alkyl, preferably $C_1$–$C_2$ alkyl) quaternary ammonium salts.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Cationic surfactants are preferably utilized at levels of from about 0.1% to about 10%, more preferably from about 0.25% to about 5%, most preferably from about 0.5% to about 2%, by weight of the composition.

CATIONIC POLYMER CONDITIONING AGENT

The compositions of the present invention can also comprise one or more cationic polymer conditioning agents. The cationic polymer conditioning agents will preferably be water soluble. Cationic polymers are typically used in the same ranges as disclosed above for cationic surfactants.

By "water soluble" cationic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least about 1.1 meq/gram, most preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp.

(Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethylallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

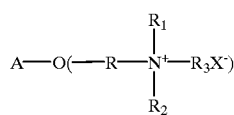

wherein: A is an anhydroglucose residual group, such as a starch or cellulose anhydroglucose residual, R is an alkylene oxyalkylene, polyoxyalkylene, or hydroxyalkylene group, or combination thereof, $R_1$, $R_2$, and $R_3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R_1$, $R_2$ and $R_3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated herein by reference.)

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g., sodium polystyrene sulfonate).

SILICONE CONDITIONING AGENTS

The compositions hereof can also include nonvolatile soluble or insoluble silicone conditioning agents. By soluble what is meant is that the silicone conditioning agent is miscible with the aqueous carrier of the composition so as to form part of the same phase. By insoluble what is meant is that the silicone forms a separate, discontinuous phase from the aqueous carrier, such as in the form of an emulsion or a suspension of droplets of the silicone.

The silicone hair conditioning agent will be used in the compositions hereof at levels of from about 0.05% to about 10% by weight of the composition, preferably from about 0.1% to about 6%, more preferably from about 0.5% to about 5%, most preferably from about 0.5% to about 3%.

Soluble silicones include silicone copolyols, such as dimethicone copolyols, e.g. polyether siloxane-modified polymers, such as polypropylene oxide, polyethylene oxide modified polydimethylsiloxane, wherein the level of ethylene and/or propylene oxide sufficient to allow solubility in the composition.

Preferred, however, are insoluble silicones. The insoluble silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone has a boiling point of at least about 260° C., preferably at least about 275° C., more preferably at least about 300° C. Such materials exhibit very low or no significant vapor pressure at ambient conditions. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 300,000 centistokes.

Silicone fluids hereof also include polyalkyl or polyaryl siloxanes with the following structure:

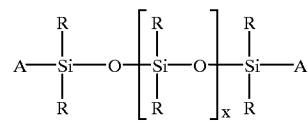

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their ViscasilR and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level should be sufficiently low to prevent solubility in the composition hereof.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone hair conditioning material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

An optional ingredient that can be included in the silicone conditioning agent is silicone resin. Silicone resins are highly crosslinked polymeric siloxane systems. The crosslinking is introduced through the incorporation of tri-functional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methyl-, phenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Silicone resins can enhance deposition of silicone on the hair and can enhance the glossiness of hair with high refractive index volumes.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO)_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

OTHER INGREDIENTS

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other conditioning agents; hair-hold polymers; detersive surfactants such as anionic, nonionic, amphoteric, and zwitterionic surfactants; additional thickening agents and suspending agents such as xanthan gum, guar gum, hydroxyethyl cellulose, methyl cellulose, hydroxyethylcellulose, starch and starch derivatives; viscosity modifiers such as methanolamides of long chain fatty acids such as cocomonoethanol amide; crystalline suspending agents; pearlescent aids such as ethylene glycol distearate; preservatives such as benzyl alcohol, methyl paraben, propyl paraben and imidazolidinyl urea; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, disobutyl adipate, butyl stearate, and propylene glycol. Such optional ingredients generally are used individually at levels from about 0.01% to about 10.0%, preferably from about 0.05% to about 5.0% by weight of the composition.

METHOD OF USE

The hair care compositions of the present invention are used in conventional ways to provide the conditioning and other benefits of the present invention. Such method of use depends upon the type of composition employed but generally involves application of an effective amount of the product to the hair, which may then be rinsed from the hair (as in the case of hair rinses) or allowed to remain on the hair (as in the case of gels, lotions, and creams). "Effective amount" means an amount sufficient enough to provide a dry combing benefit. In general, from about 1 g to about 50 g is applied to the hair on the scalp. The composition is distributed throughout the hair, typically by rubbing or massaging the hair and scalp. Preferably, the composition is applied to wet or damp hair prior to drying of the hair. After such compositions are applied to the hair, the hair is dried and styled in accordance with the preference of the user. In the alternative, the composition is applied to dry hair, and the hair is then combed or styled in accordance with the preference of the user.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components may come from suppliers as dilute solutions. The levels given reflect the weight percent of the active material, unless otherwise specified.

Examples I–V

Hair rinse compositions of the present invention are prepared as follows:

| Component (Wt. %) | Ex. I | Ex. II | Ex. III | Ex. IV | EX. V |
|---|---|---|---|---|---|
| Oleyl Alcohol | 1.0 | 1.0 | 1.0 | 1.0 | 0.25 |
| PEG-7M[1] | 2.0 | 1.0 | — | 1.0 | — |
| PEG-2M[2] | — | — | 1.0 | — | 1.00 |
| Polydimethylsiloxane[3] | 4.20 | 4.2 | 4.2 | 4.2 | 4.2 |
| Silicone Resin[4] | 0.25 | 0.25 | 0.25 | 0.25 | — |
| Pentaphenyl Trimethyl Trisiloxane[5] | 0.38 | 0.38 | 0.38 | 0.38 | — |
| DL Panthenol | 0.04 | 0.04 | 0.04 | 0.04 | .04 |
| Panthenyl Ethyl Ether | 0.34 | 0.34 | 0.34 | 0.34 | .34 |
| Fragrance | 0.3 | 0.35 | 0.35 | 0.35 | .35 |
| Kathon ™ CG[6] | 0.03 | 0.03 | 0.03 | 0.03 | .03 |
| Cetyl Alcohol | 1.2 | 1.8 | 1.8 | 1.2 | 1.2 |
| Stearyl Alcohol | 0.8 | 1.2 | 1.2 | 0.8 | 0.8 |
| Ditallow Dimethyl Ammonium Chloride | 0.75 | 0.75 | 0.75 | 0.75 | 0.75 |
| Stearamidopropyl Dimethylamine | 1.0 | 1.0 | 1.0 | 1.0 | 1.0 |
| Glycerol Monostearate | 0.25 | 0.25 | 0.25 | 0.25 | 0.25 |
| Citric Acid | 0.19 | 0.22 | 0.22 | 0.19 | 0.22 |
| Hydroxyethyl Cellulose | — | 0.25 | 0.25 | — | 0.25 |
| Mineral Oil | — | — | — | — | 0.25 |
| Water | q.s | q.s | q.s | q.s | q.s |

[1]PEG-7M is Polyethylene Glycol where n has an average value of about 7,000 and is commercially available under the tradename of Polyox WSR ® N-750 from Union Carbide.
[2]PEG-2M is Polyethylene Glycol where n has an average value of about 2,000 and is commercially available under the tradename of Polyox WSR ® N-10 from Union Carbide.
[3]An 85%/15% (wt. basis) mixture of D5 Cyclomethicone and dimethicone gum (weight average molecular weight of about 400,000 to about 600,000).
[4]Polytrimethyl hydrosilylsilicate, added as a 50 wt. % solution in decamethylcyclopentasiloxane, General Electric Silicone Products, SS 4320.
[5]Dow Corning 705, Dow Corning Corp. (Midland, MI, USA).
[6]Methylchloroisothiazoline (and) methylisothiazoline, a preservative from Rohm & Haas Co., (Philadelphia PA, USA).

Examples VI and VII

Hair rinse compositions of the present invention are prepared as follows:

| Component (Wt %) | Ex. VI | Ex. VII |
|---|---|---|
| Oleyl Alcohol | 0.25 | 1.0 |
| PEG-7M[1] | 1.0 | — |
| PEG-14M[2] | — | 0.25 |
| Polydimethylsiloxane[3] | 4.20 | 4.2 |
| Silicone Resin[4] | 0.25 | 0.25 |
| Pentaphenyl Trimethyl Trisiloxane[5] | 0.38 | 0.38 |
| DL Panthenol | 0.04 | 0.04 |
| Panthenyl Ethyl Ether | 0.34 | 0.34 |
| Fragrance | 0.35 | 0.35 |
| Kathon ™ CG[6] | 0.03 | 0.03 |
| Cetyl Alcohol | 1.8 | 1.8 |
| Stearyl Alcohol | 1.2 | 1.2 |
| Ditallow Dimethyl Ammonium Chloride | 0.75 | 0.75 |
| Stearamidopropyl Dimethylamine | 1.0 | 1.0 |
| Glycerol Monostearate | 0.25 | 0.25 |
| Citric Acid | 0.22 | 0.22 |
| Hydroxyethyl Cellulose | 0.25 | 0.25 |
| Water | q.s | q.s |

[1]PEG-7M is Polyethylene Glycol where n has an average value of about 7,000 and is commercially available under the tradename of Polyox WSR ® N-750 from Union Carbide.
[2]PEG-2M is Polyethylene Glycol where n has an average value of about 2,000 and is commercially available under the tradename of Polyox WSR ® N-10 from Union Carbide.
[3]An 85%/15% (wt. basis) mixture of D5 Cyclomethicone and dimethicone gum (weight average molecular weight of about 400,000 to about 600,000).
[4]Polytrimethyl hydrosilylsilicate, added as a 50 wt. % solution in decamethylcyclopentasiloxane, General Electric Silicone Products, SS 4320.
[5]Dow Corning 705, Dow Corning Corp. (Midland, MI, USA).
[6]Methylchloroisothiazoline (and) methylisothiazoline, a preservative from Rohm & Haas Co., (Philadelphia PA, USA).

For each of the above examples, a silicone premix is prepared by mixing: the polydimethylsiloxane, silicone resin, and pentaphenyl trimethyltrisiloxane in a tank.

For Examples I–V, the PEG is added to ambient water and thereafter mixed. Then this mixture is heated to about 80° C. The following ingredients are then added, sequentially, with agitation between each addition: ditallow dimethyl ammonium chloride, oleyl alcohol, cetyl alcohol, stearyl alcohol, stearamidopropyl dimethylamine, and glyceryl monostearate. Cool the batch to about 49° C. Then the following ingredients are added, sequentially, with agitation between each addition: silicone premix, citric acid, panthenol, panthenyl ethyl ether, perfume, and Kathon™ CG. Cool the composition to a temperature of from about 25° C. to about 35° C.

For Examples II and VII, the hydroxyethyl cellulose is added to ambient water and agitated. PEG-7M or PEG-14M is added and the mixture is heated to about 80° C. The following ingredients are then added, sequentially, with agitation between each addition: ditallow dimethyl ammonium chloride, cetyl alcohol, stearyl alcohol, stearamidopropyl dimethylamine, and glyceryl monostearate. Cool the batch to about 49° C. Then the following ingredients are added, sequentially, with agitation between each addition: silicone premix, citric acid, panthenol, panthenyl ethyl ether, perfume, Kathon™ CG, and oleyl alcohol. Cool the composition to a temperature of from about 25° C. to about 35° C.

For Examples II, III and V, the hydroxyethyl cellulose is added to ambient water and agitated. The PEG-2M or PEG-7M is added and the mixture is heated to about 80° C. The following ingredients are then added, sequentially, with agitation between each addition: ditallow dimethyl ammonium chloride, cetyl alcohol, stearyl alcohol, stearamidopropyl dimethylamine, and glyceryl monostearate. Cool the batch to about 49° C. Then the following ingredients are added, sequentially, with agitation between each addition: silicone premix, citric acid, panthenol, panthenyl ethyl ether, perfume, Kathon™ CG, and oleyl alcohol. Cool the composition to a temperature of from about 25° C. to about 35° C.

What is claimed is:

1. A hair care composition comprising:
   (a) from about 0.1% to about 10% by weight, of a low melting point fatty alcohol having a melting point of 30° C. or lower;
   (b) from about 0.2% to about 10% by weight, of a polymer of ethylene oxide, propylene oxide, and mixtures thereof, having the formula:

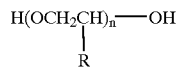

wherein R is selected from the group consisting of H, methyl, and mixtures thereof; and n has an average value of from about 2,000 to about 14,000;
   (c) from 0% to about 20% by weight, of a conditioning agent selected from the group consisting of cationic surfactants, cationic polymers, nonvolatile silicones, nonvolatile hydrocarbons, saturated $C_{14}$ to $C_{22}$ straight chain fatty alcohols, nonvolatile hydrocarbon esters, and mixtures thereof; and
   (d) from about 50% to about 99.8% by weight, water.

2. The composition of claim 1 wherein the low melting point fatty alcohol is selected from the group consisting of unsaturated $C_8$–$C_{22}$ straight chain fatty alcohols, saturated $C_{12}$–$C_{18}$ branched chain fatty alcohols, saturated $C_8$–$C_{12}$ straight chain fatty alcohols, and mixtures thereof.

3. The composition of claim 2 wherein the low melting point fatty alcohol has a melting point of 25° C. or lower.

4. The composition of claim 3 wherein the fatty alcohol is selected from the group consisting of unsaturated $C_{16}$–$C_{18}$ straight chain fatty alcohols, $C_{14}$–$C_{18}$ branched chain fatty alcohols, and mixtures thereof.

5. The composition of claim 4 wherein the fatty alcohol is oleyl alcohol.

6. The composition of claim 1 wherein n has an average value of from about 5,000 to about 9,000.

7. The composition of claim 6 wherein the low melting point fatty alcohol is selected from the group consisting of unsaturated $C_8$–$C_{22}$ straight chain fatty alcohols, saturated $C_{12}$–$C_{18}$ branched chain fatty alcohols, saturated $C_8$–$C_{12}$ straight chain fatty alcohols, and mixtures thereof.

8. The composition of claim 7 wherein the low melting point fatty alcohol has a melting point of 25° C. or lower.

9. The composition of claim 8 wherein the fatty alcohol is selected from the group consisting of unsaturated $C_{16}$–$C_{18}$ straight chain fatty alcohols, $C_{14}$–$C_{18}$ branched chain fatty alcohols, and mixtures thereof.

10. The composition of claim 9 wherein the fatty alcohol is oleyl alcohol.

11. The composition of claim 1 wherein R is H and n has an average value of from about 5,000 to about 9,000.

12. The composition of claim 11 wherein n has an average value of from about 6,000 to about 8,000.

13. The composition of claim 12 wherein the low melting point fatty alcohol is selected from the group consisting of unsaturated $C_8$–$C_{22}$ straight chain fatty alcohols, saturated $C_{12}$–$C_{18}$ branched chain fatty alcohols, saturated $C_8$–$C_{12}$ straight chain fatty alcohols, and mixtures thereof.

14. The composition of claim 13 wherein the low melting point fatty alcohol has a melting point of 25° C. or lower.

15. The composition of in claim 14 wherein the fatty alcohol is selected from the group consisting of unsaturated $C_{16}$–$C_{18}$ straight chain fatty alcohols, $C_{14}$–$C_{18}$ branched chain fatty alcohols, and mixtures thereof.

16. The composition of claim 15 wherein the fatty alcohol is oleyl alcohol.

17. The composition of claim 1 comprising:
   (a) from about 0.25% to about 1% by weight, of a low melting point fatty alcohol having a melting point of 30° C. or lower;
   (b) from about 0.5% to about 3% by weight, of a polymer of ethylene oxide having the formula:

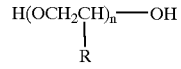

wherein R is H and n has an average value of from about 5,000 to about 9,000; and
   (c) from 0.1% to about 20% by weight, of a conditioning agent selected from the group consisting of cationic surfactants, cationic polymers, nonvolatile silicones, nonvolatile hydrocarbons, saturated $C_{14}$ to $C_{22}$ straight chain fatty alcohols, nonvolatile hydrocarbon esters, and mixtures thereof.

18. The composition of claim 17 wherein the conditioning agent is selected from the group consisting of cationic surfactants, saturated $C_{14}$ to $C_{22}$ straight chain fatty alcohols, and mixtures thereof.

19. The composition of claim 18 wherein the composition comprises from about 0.5% to about 2% by weight of a quaternary ammonium cationic surfactant.

20. The composition of claim 19 wherein the quaternary ammonium surfactant is selected from the group consisting of ditallow dimethyl quaternary ammonium compound, monotallow trimethyl quaternary ammonium compound, dicetyl dimethyl quaternary ammonium compound, and mixtures thereof.

21. The composition of claim 18 wherein the composition comprises from about 0.5% to about 5% of a saturated $C_{14}$ to $C_{22}$ straight chain fatty alcohol.

22. A method for conditioning hair comprising applying an effective amount of the composition of claim 1 to the hair for enhanced dry combing.

23. A method for conditioning hair comprising applying an effective amount of the composition of claim 17 to the hair for enhanced dry combing.

* * * * *